(12) United States Patent
Hickey

(10) Patent No.: US 8,563,299 B2
(45) Date of Patent: Oct. 22, 2013

(54) MOVING BED BIOFILM REACTOR (MBBR) PROCESS FOR CONVERSION OF SYNGAS COMPONENTS TO LIQUID PRODUCTS

(71) Applicant: Robert Hickey, Okemos, MI (US)

(72) Inventor: Robert Hickey, Okemos, MI (US)

(73) Assignee: Coskata, Inc., Warrenville, IL (US)

( * ) Notice: Subject to any disclaimer, the term of this patent is extended or adjusted under 35 U.S.C. 154(b) by 0 days.

(21) Appl. No.: 13/782,480

(22) Filed: Mar. 1, 2013

(65) Prior Publication Data

US 2013/0164802 A1    Jun. 27, 2013

Related U.S. Application Data

(63) Continuation-in-part of application No. 11/833,864, filed on Aug. 3, 2007.

(51) Int. Cl.
*C12M 1/14*    (2006.01)
*C12M 3/04*    (2006.01)

(52) U.S. Cl.
USPC .......... 435/299.1; 435/41; 435/136; 435/157; 435/161; 435/297.1

(58) Field of Classification Search
USPC ............. 435/41, 136, 157, 161, 170, 252.1, 435/289.1, 294.1, 296.1, 297.1, 297.4, 435/299.1; 210/242.2, 607, 649, 704, 805
See application file for complete search history.

(56) References Cited

U.S. PATENT DOCUMENTS 5,205,935 A * 4/1993 Ruocco .......................... 210/603
5,254,253 A * 10/1993 Behmann ...................... 210/607

FOREIGN PATENT DOCUMENTS

WO    WO02/08438    *    1/2002

OTHER PUBLICATIONS

Bjorn et al, "Design and operation of the Kaldnes moving bed biofilm reactors", Aquacultural Engineering, vol. 34, issue 3, pp. 322-331, May 2006.*

* cited by examiner

*Primary Examiner* — Michael Marcheschi
*Assistant Examiner* — Shanta G Doe

(57) ABSTRACT

A process for converting a feed gas containing at least one of CO, $CO_2$, and/or $H_2$ to a liquid product using biomass that grow on the surface of carriers suspended in a fermentation broth within the vessel of a moving bed bioreactor (MMBR). An injector is used to at least partially dissolved the feed gas in the fermentation broth, at least partially entrain the gas in the broth as microbubbles and to introduce the mixture of the entrained gas and broth into the vessel in a substantially horizontal direction. The injection of the mixture creates eddy current in the surrounding liquid for thoroughly mixing the fermentation broth in the vessel and for keeping the biomass carrier moving to provide sufficient shear so as to maintain a biofilm thickness on the carrier in a desirable range.

10 Claims, 4 Drawing Sheets

MOVING BED BIOFILM REACTOR (MBBR) PROCESS FOR CONVERSION OF SYNGAS COMPONENTS TO LIQUID PRODUCTS

CROSS-REFERENCE TO RELATED APPLICATIONS

This application is a Continuation-In-Part application that claims the benefit of U.S. Non-Provisional patent application Ser. No. 11/833,864 filed Aug. 3, 2007, which is incorporated in its entirety herein by this reference.

FIELD OF THE INVENTION

This invention relates to the biological conversion of CO and mixtures of $CO_2$ and $H_2$ to liquid products.

BACKGROUND

The conversion of gas streams into liquid products by contact with a conversion medium in a liquid phase is well practiced in many fields. Where the solubility of the gas stream is limited, contacting and conversion of the gas stream of requires that the gas stream be disbursed within a liquid medium as a fine dispersion of micro bubbles to increase the mass transfer between the gas phase and the liquid phase. Getting the gas into the liquid phase is energy intensive and ways are continually sought to reduce the expense of providing the necessary energy to create a two phase dispersion of the gas and liquid.

A wide variety of devices are known for the dispersion of gas and liquid medium. Such devices include venturi injectors, slot injectors, or jet injectors and other high pressure mixers. Such gas transfer devices have found widespread use in a variety of fields including those of wastewater treatment and fermentation.

The field of fermentation is one in which particular application of this is of interest due to the increased emphasis on the conversion of renewable sources into liquid products such as motor fuels Biofuels production for use as liquid motor fuels or for blending with conventional gasoline or diesel motor fuels is increasing worldwide. Such biofuels include, for example, ethanol and n-butanol. One of the major drivers for biofuels is their derivation from renewable resources by fermentation and bioprocess technology. Conventionally, biofuels are made from readily fermentable carbohydrates such as sugars and starches. For example, the two primary agricultural crops that are used for conventional bioethanol production are sugarcane (Brazil and other tropical countries) and corn or maize (U.S. and other temperate countries). The availability of agricultural feed stocks that provide readily fermentable carbohydrates is limited because of competition with food and feed production, arable land usage, water availability, and other factors. Consequently, lignocellulosic feed stocks such as forest residues, trees from plantations, straws, grasses and other agricultural residues may become viable feed stocks for biofuel production. However, the very heterogeneous nature of lignocellulosic materials that enables them to provide the mechanical support structure of the plants and trees makes them inherently recalcitrant to bioconversion. Also, these materials predominantly contain three separate classes of components as building blocks: cellulose ($C_6$ sugar polymers), hemicellulose (various $C_5$ and $C_6$ sugar polymers), and lignin (aromatic and ether linked hetero polymers). For example, breaking down these recalcitrant structures to provide fermentable sugars for bioconversion to ethanol typically requires pretreatment steps together with chemical/enzymatic hydrolysis. Furthermore, conventional yeasts are unable to ferment the $C_5$ sugars to ethanol and lignin components are completely unfermentable by such organisms. Often lignin accounts for 25 to 30% of the mass content and 35 to 45% of the chemical energy content of lignocellulosic biomass. For all of these reasons, processes based on a pretreatment/hydrolysis/fermentation path for conversion of lignocellulose biomass to ethanol, for example, are inherently difficult and often uneconomical multi-step and multi conversion processes.

An alternative technology path is to convert lignocellulosic biomass to syngas (also known as synthesis gas, primarily a mix of CO, $H_2$ and $CO_2$ with other components such as $CH_4$, $N_2$, $NH_3$, $H_2S$ and other trace gases) and then ferment this gas with anaerobic microorganisms to produce biofuels such as ethanol, n-butanol or chemicals such as acetic acid, butyric acid and the like. This path can be inherently more efficient than the pretreatment/hydrolysis/fermentation path because the gasification step can convert all of the components to syngas with good efficiency (e.g., greater than 75%), and some strains of anaerobic microorganisms can convert syngas to ethanol, n-butanol or other chemicals with high (e.g., greater than 90% of theoretical) efficiency. Moreover, syngas can be made from many other carbonaceous feedstocks such as natural gas, reformed gas, biogas, peat, petroleum coke, coal, solid waste and land fill gas, making this a more universal technology path.

However, this technology path requires that the syngas components CO and $H_2$ be efficiently and economically dissolved in the aqueous medium and transferred to anaerobic microorganisms that convert them to the desired products. And very large quantities of these gases are required. For example, the theoretical equations for CO or $H_2$ to ethanol are:

$$6CO+3H_2O \rightarrow C_2H_5OH+4CO_2$$

$$6H_2+2CO_2 \rightarrow C_2H_5OH+3H_2O$$

Thus 6 moles of relatively insoluble gases such as CO or $H_2$ have to transfer to an aqueous medium for each mole of ethanol. Other products such as acetic acid and n-butanol have similar large stoichiometric requirements for the gases.

Furthermore, the anaerobic microorganisms that bring about these bioconversions generate very little metabolic energy from these bioconversions. Consequently they grow very slowly and often continue the conversions during the non-growth phase of their life cycle to gain metabolic energy for their maintenance. Many devices and equipment are used for gas transfer to microorganisms in fermentation and waste treatment applications. These numerous bioreactors all suffer from various drawbacks. In most of these conventional bioreactors and system, agitators with specialized blades or configurations are used. In some others such as gas lift or fluidized beds, liquids or gases are circulated via contacting devices. The agitated vessels require a lot of mechanical power often in the range of 4 to 10 KW per 1000 liters—uneconomical and unwieldy for large scale fermentations that will be required for such syngas bioconversions. The fluidized or fluid circulating system cannot economically provide the required gas dissolution rates. Furthermore, most of these reactors in the process are configured for use with microorganisms in planktonic or suspended form i.e. they exist as individual cells in liquid medium.

In the field of fermentation the use of gas injection devices is known to disperse gas streams into liquids. U.S. Pat. No. 4,426,450 discloses a fermentation vessel that uses a plurality of jet injectors to mix air and a fermentation broth in the bottom of a fermentation vessel. The '450 reference requires a gas stream at sufficient pressure to overcome the hydraulic pressure of the liquid in the vessel.

Furthermore, for the suspended cultures to get high yields and production rates the cell concentrations in the bioreactor need to be high and this requires some form of cell recycle or retention. Conventionally, this is achieved by filtration of the fermentation broth through microporous or nonporous membranes, returning the cells and purging the excess. These systems are expensive and require extensive maintenance and cleaning of the membranes to maintain the fluxes and other performance parameters. Cell retention by formation of biofilms is a very good and often inexpensive way to increase the density of microorganisms in bioreactors. This requires a solid matrix with large surface area for the cells to colonize and form a biofilm that contains the metabolizing cells in a matrix of biopolymers that the cells generate. Trickle bed and some fluidized bed bioreactors make use of biofilms to retain microbial cells on solid surfaces while providing dissolved gases in the liquid by flow past the solid matrix. They suffer from either being very large or unable to provide sufficient gas dissolution rates.

Moving Bed Biofilm Reactors (MBBR) have been shown to be high-rate, compact system for wastewater treatment, particularly where slow growing organisms are involved. Hallvard, Odegaard describes the use of MBBR system for the treatment of wastewater in Innovations in wastewater treatment: the moving bed biofilm process—Water and Science & Technology Vol 53 No 9 pp 17-32. These biofilm type rectors are especially compatible with highly efficient (in terms of both gas transfer efficiency [power per mass of gas transferred] and dissolution efficiency) such as jet and/or slot aerators/gas transfer devices. The combination of the MBBR process and these gas transfer devices overcomes the problems associate with alternate approaches described above.

It is also highly desirable to retain the microorganisms in the form of a biofilm. It is known that single organism systems are susceptible to phase attack. However, forming a biofilm is one known method to reduce susceptibility of microorganisms to a phage attack.

SUMMARY OF THE INVENTION

The instant invention involves using a buoyant or suspended carrier as a media for supported the biomass in what is termed a MBBR. In this process the fermenting biomass adheres to and grows on the surfaces of an inert biomass carrier media as biofilm. The process delivers gaseous substrates CO and/or $CO_2/H_2$ via any device that will promote high gas dissolution and utilization. Such devices include gas spargers and preferably a high efficiency gas transfer process such as jet or slot aerator/gas transfer devices. The gas injection device is positioned on a fermentation vessel in manner to provide direct injection of the gas and liquid into direct and immediate contact with microorganisms and fermentation broth. In addition the gas injector normally serves the additional function of creating eddy currents in the surrounding liquid for thoroughly mixing the contents of the fermentation vessel. Gas bubbles from the gas delivery device will rise to the liquid surface and provide additional mixing and gas dissolution. Desirably the fermentation vessel has sufficient depth to ensure high gas dissolution and utilization. Typically the fermentation vessel has a minimum depth of 9 meters that is wetted by the fermentation broth and achieves at least 80% gas dissolution and consumption. In a preferred form of this invention at least a portion of the microbubbles, after horizontal injection, will change direction and travel vertically through the fermentation broth for a distance of at least 9 meters feet. Other microbubbles may be absorbed into the fermentation broth before reaching the surface of the fermentation broth in the vessel.

The wetted depth of the fermentation broth provides the working volume where the motion of gas and liquid keeps the biomass carrier moving. The biomass carrier is typically maintained in the reactor via an outlet sieve or other suitable screening device. The turbulence created by any flow of gas and/or liquid through the vessel can also provide sufficient shear so as to maintain the biofilm thickness on the biomass carrier in the desirable range.

In a more specific embodiment this invention is a process for converting a feed gas containing at least one of CO, $H_2$ and $CO_2$ and a mixture of $CO_2$, $H_2$ and CO to a liquid product. The process passes a feed gas into a vessel that retains a fermentation broth and microorganisms therein under anaerobic conditions with the fermentation broth supplying nutrients to the microorganisms that produce a liquid product from the feed gas. The feed gas and liquid medium pass into an injector to at least partially entrain the feed gas into the liquid medium as microbubbles and delivering the entrained feed gas and liquid medium to the fermentation broth as a plume. The plume gets injected into the vessel in a substantially horizontal direction. The term "substantially horizontal" means that the discharge direction of the injector along which it directs the gas and liquid, typically as plume varies by no more 35 degrees from the horizontal, preferably by no more than 30 degrees from the horizontal. The process retains the microorganism in the vessel on inert carriers having a surface supporting a biofilm of the microorganisms in the vessel. The carriers are arranged for circulation throughout the fermentation broth in the vessel. Circulation of the biomass carriers containing the microorganism and the broth in the vessel puts from time to time a portion of the carrier and the broth from in direct and immediate contact with the plume of feed gas and liquid medium at the location where the feed gas and liquid medium enter the vessel in a substantially horizontal direction. The plume passes upward and horizontally through the vessel after the substantially horizontal injection of the liquid medium and feed gas through the feed injector so that at least a part of the plume travels in a horizontal direction. Depending on the diameter of the vessel, the plume may travel across the width or diameter of the vessel, or with somewhat larger vessels at least half way across the width or diameter of the vessel. Very large vessels typically have substantially horizontal injection at multiple points around the circumference of the vessel so that broth and microorganisms and feed gas mix to deliver feed gas across the full cross section of the vessel. The process then withdraws fermentation broth containing liquid products from the vessel.

In other embodiments the process withdraws the fermentation broth through a carrier retainer to impede the withdrawal of the carrier material with the broth. The process is particularly suited for making ethanol. It has been observed that the presence of oxygenates such as ethanol in the fermentation media at as low as 1% (weight/volume) has a profound effect on gas transfer efficiency. The change in surface tension results in smaller bubbles being generated and therefore a significantly greater surface area of gas bubbles exposed to the liquid. The result is transfer rates of up to 3 times that observed for clean water.

The result of combining a MBBR process having a gaseous feed with a highly efficient gas transfer process, preferably such as a jet or slot aerators/gas transfer devices, results in an economical and high product volumetric production rate process for production of liquid products. One additional advantage of the slot and jet gas transfer devices is that they are relatively clog free and treatment of the syngas components for small particulates is not necessarily required.

DETAILED DESCRIPTION OF THE INVENTION

Figure 1:
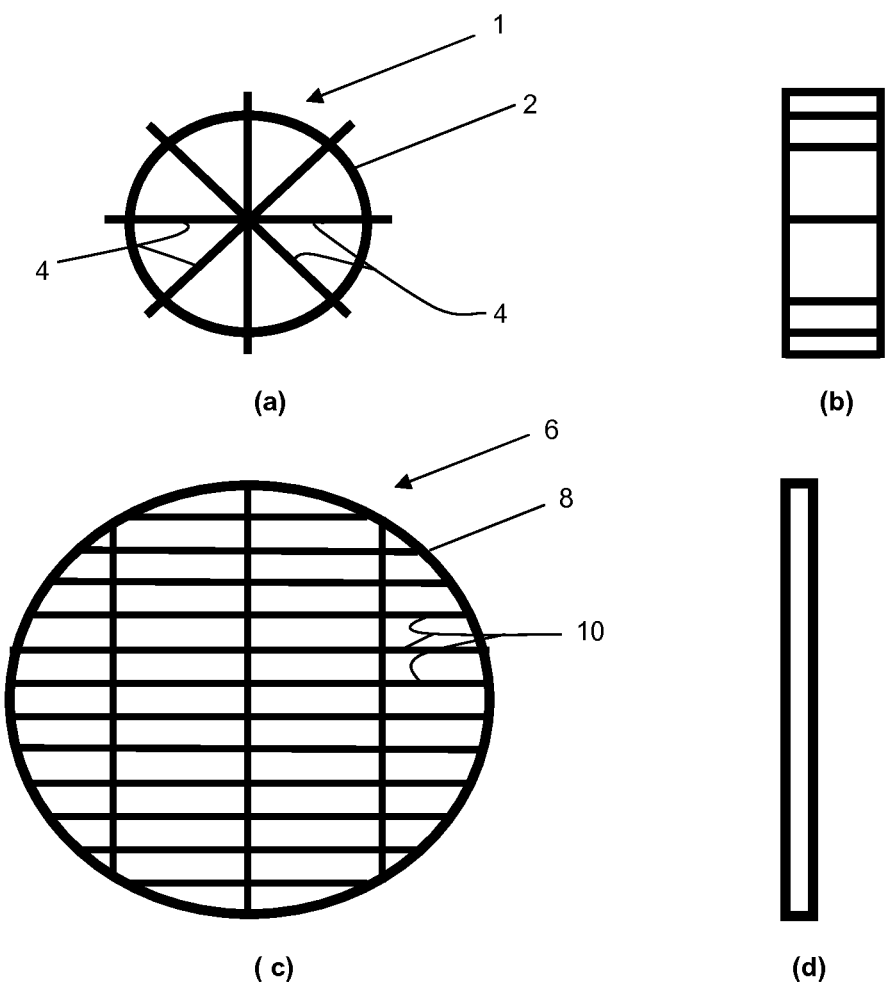
FIG. 1 is a schematic drawing showing two different types of media for the MBBR biomass carrier.

Bioconversions of CO and $H_2/CO_2$ to acetic acid, ethanol and other products are well known. For example, in a recent book concise description of biochemical pathways and energetics of such bioconversions have been summarized by Das, A. and L. G. Ljungdahl, Electron Transport Process in Acetogens and by Drake, H. L. and K. Kusel, Diverse Physiologic Potential of Acetogens, appearing respectively as Chapters 14 and 13 of Biochemistry and Physiology of Anaerobic Bacteria, L. G. Ljungdahl eds, Springer (2003). Any suitable microorganisms that have the ability to convert the syngas components: CO, $H_2$, $CO_2$ individually or in combination with each other or with other components that are typically present in syngas may be utilized. Suitable microorganisms and/or growth conditions may include those disclosed in U.S. patent application Ser. No. 11/441,392, filed May 25, 2006, entitled "Indirect Or Direct Fermentation of Biomass to Fuel Alcohol," which discloses a biologically pure culture of the microorganism *Clostridium carboxidivorans* having all of the identifying characteristics of ATCC no. BAA-624; and U.S. patent application Ser. No. 11/514,385 filed Aug. 31, 2006 entitled "Isolation and Characterization of Novel *Clostridial* Species," which discloses a biologically pure culture of the microorganism *Clostridium ragsdalei* having all of the identifying characteristics of ATCC No. BAA-622; U.S. Pat. No. 8,143,037 entitled "Ethanolognic *Clostridium* species, *Clostridum coskatii*" which discloses a biologically pure culture of the microorganism *Clostridium coskatii* and *Clostridium autoethanogenum* (Abrini et al., 1994) having all of the identifying characteristics of (DSMZ NO. 10061) all of which are incorporated herein by reference in their entirety. *Clostridium carboxidivorans* may be used, for example, to ferment syngas to ethanol and/or n-butanol. *Clostridium ragsdalei* may be used, for example, to ferment syngas to ethanol.

Suitable microorganisms and growth conditions include the anaerobic bacteria *Butyribacterium methylotrophicum*, having the identifying characteristics of ATCC 33266 which can be adapted to CO and used and this will enable the production of n-butanol as well as butyric acid as taught in the references: "Evidence for Production of n-Butanol from Carbon Monoxide by *Butyribacterium methylotrophicum*," Journal of Fermentation and Bioengineering, vol. 72, 1991, p. 58-60; "Production of butanol and ethanol from synthesis gas via fermentation," FUEL, vol. 70, May 1991, p. 615-619. Other suitable microorganisms include *Clostridium Ljungdahli*, with strains having the identifying characteristics of ATCC 49587 (U.S. Pat. No. 5,173,429) and ATCC 55988 and 55989 (U.S. Pat. No. 6,136,577) and this will enable the production of ethanol as well as acetic acid. All of these references are incorporated herein in their entirety.

The instant invention uses MBBR in concert with highly efficient gas transfer devices, such as jet or slot aerators/gas transfer devices, to dissolve gases into the liquid phase for delivering CO and/or a mixture of $H_2$ and $CO_2$ to the anaerobic microorganism maintained as a biofilm on inert biomass carrier media. The microorganisms in the biofilm use the CO and/or $H_2/CO_2$ in the gas and transform them into ethanol and other liquid products. The biomass support media allows the slow growing anaerobic microorganisms to be maintained in the fermentation vessel at concentrations well above what is possible with suspended culture. The result is a highly efficient and economical conversion of the CO and/or $CO_2/H_2$ to liquid products.

This invention can be used with any stream that contains a suitable concentration of syngas components. Suitable streams will preferably contain a minimum of 10 wt. % CO and/or $H_2$. The process will normally operate under anaerobic conditions.

Suitable media for the MBBR biomass carrier made from polymers have been recently developed and commercialized for wastewater treatment and purification applications. Typically these media are made from hydrophobic polymers such as polyethylene or polypropylene which are processed or formed to create a highly protected external or internal surface area for biofilm attachment and accumulation of high biomass concentrations. A protected surface is one in which the structure of the media minimizes direct contact between the microorganisms and other pieces of media. Several commercial organizations supply such media primarily as extruded cylindrical media.

Suitable media is commercially available from a number of companies including AnoxKaldnes, Siemens/Aqwise and Mutag. Some characteristics of the different media from AnoxKaldnes is given in the Table 1 below.

TABLE 1

Partial List of Commercially available MBBR media

| Company | Model | Length (mm) | Diameter (mm) | Protected surface ($m^2/m^3$) | Total surface ($m^2/m^3$) |
|---|---|---|---|---|---|
| AnoxKaldnes | K1 | 7 | 9 | 500 | 800 |
| | K3 | 12 | 25 | 500 | 600 |
| | Natrix C2 | 30 | 36 | 220 | 265 |
| | Natrix M2 | 50 | 64 | 200 | 230 |
| | Biofilm-Chip M | 2.2 | 48 | 1200 | 1400 |
| | Biofilm-Chip P | 3 | 45 | 900 | 990 |
| Hydroxyl | ActiveCell | 15 | 22 | 448 | 588 |

The media employed are generally extruded cylindrical type media made from polypropylene, polyethylene or recycled plastics. These materials typically provide the media with a relative density of 0.9 to 0.98 with respect to the fermentation broth and a ratio of protected surface/total surface of at least 60%. The design of the media is such to maximize the overall surface area for attachment of a biofilm. Accordingly the internal or protected surface area will generally be at least 60% of the total surface area of the media. The media volume shall comprise between 30% and 70% of the wetted volume of the fermentation vessel.

FIGS. 1(a)-1(d) illustrate two examples of the many suitable structures that can supply the moving media for support of biofilms. FIG. 1(a) depicts the transverse view of a spoke and hub type media. FIG. 1(a) shows a cylinder 2 intersecting eight parallel vanes 4 that emanate from the center point of cylinder 2 and protrude outside its circumference. The internal sectors defined by the vanes and inner cylinder wall provide the interior surface for retention of a biofilm. FIGS. 1(c) and 1(d) illustrate another geometry for a support media 6 wherein an outer cylinder supports a rectangular grid work 10 of internal surfaces for the supporting a biofilm. FIGS. 1(b) and 1(d) depicts side views of the medial of FIGS. 1(a) and 1(c) respectively which typically have a nominal diameter of from 5 to 50 mm and a width between 2 and 50 mm.

Figure 2:
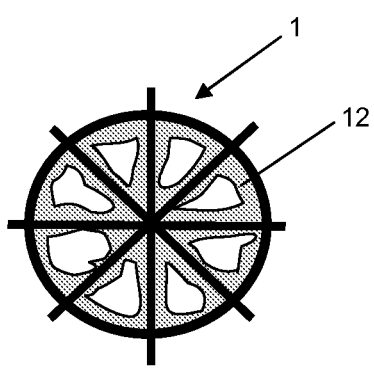
FIG. 2 shows the carrier media of FIGS. 1(a) and (b) with attached biofilm

FIG. 2 shows a biofilm growing on the support media 1 of FIGS. 1(a) & 1(b). The support media grows on the interior surfaces of the media. The internal vane structure blocks entry of surrounding carrier media to protect the biofilm while also providing additional surface for support of the biofilm.

Figure 3:
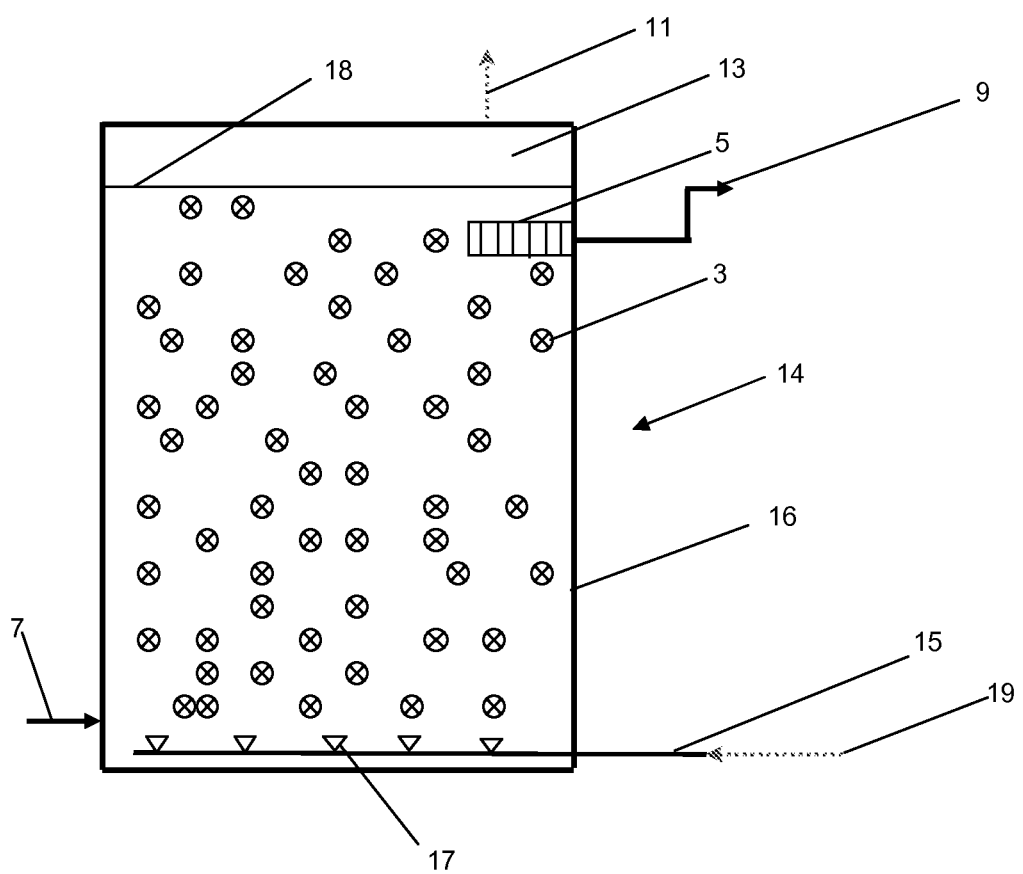
FIG. 3 is a schematic drawing shows combination of a typical MBBR reactor and conventional gas sparging aerator for gas transfer

FIG. 3 schematically shows a support media 3 suspended in a fermentation broth held by a fermentation vessel 16 of an MBBR process 14. A conventional gas sparger 17, of the type typically used for aeration, injects a feed gas 19 containing at least one of CO or a mixture of $CO_2$ and $H_2$ into the fermentation broth. The dispersed feed gas at least partially dissolves into the fermentation broth as it travels upwardly towards its liquid surface 18. Gas recovery chamber 13 collects any residual feed gas and gaseous fermentation outputs for recovery as stream 11. Stream 11 can undergo separation of gas components for recovery and/or recycle to stream 19 as desired.

The fermentation vessel maintains the fermentation broth and media at optimal metabolic conditions for the expression of the desired liquid products by the microorganisms. These conditions typically include a pressure of 1 to 5 bar and temperature of from 20 to 50.degree. C. within the fermentation vessel.

The dissolved feed gas feeds a biofilm that grows on support media 3 to produce the liquid products of this invention. A sieve device 5 screens the support media from flowing into an outlet 9 that recovers the liquid products from the vessel 16. Preferably the sieve and outlet withdraw liquid from the upper section of the vessel but may withdraw liquid from any location at or below liquid level 18.

The distance between the liquid level 18 and the bottom of vessel 16 defines the wetted depth of the MBBR process. Most applications will require a minimum wetted depth of at least 9 meters and wetted depths greater than 15 meters are preferred.

Liquid recovered via outlet 9 typically undergoes separation in a product recovery section (not shown) to recover liquid products. The product recovery section that removes the desirable product from liquid taken by outlet 9, while leaving substantial amounts of water and residual nutrients in the treated stream, part of which is returned to the vessel 16 via line 7. A nutrient feed may be added via to the broth as needed to compensate for the amount of water removed and to replenish nutrients. The nutrient feed may enter vessel 16 directly or via line 7.

Figure 4:
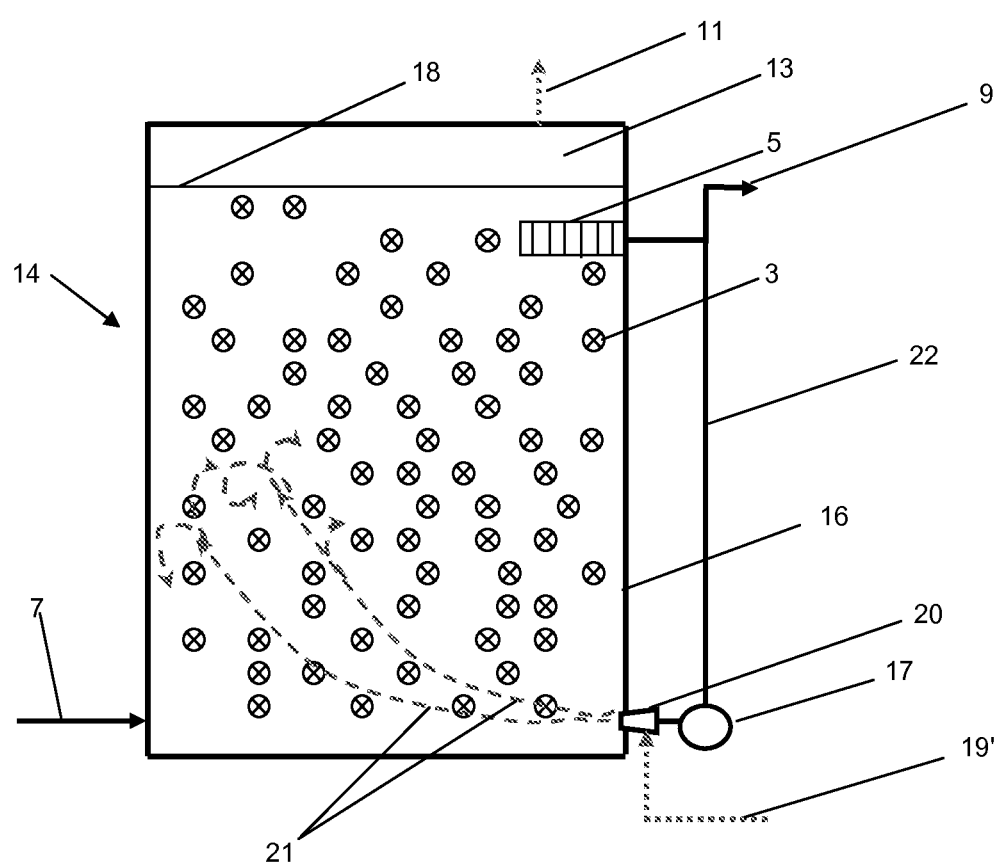
FIG. 4 is a schematic drawing shows combination of a typical MBBR reactor and slot aerator for gas transfer.

FIG. 4 depicts a generalized view of a flow arrangement similar to that of FIG. 3 except for the substitution of the conventional sparger 17 with a jet aerator 20. The jet aerator 20 provides a high velocity "throat" or contact chamber 23 that educts the feed gas 19' comprising CO and/or $CO_2/H_2$ into intimate contact with fermentation broth withdrawn from outlet 9. A line 22 transfer the broth from outlet 9 to a pump 17 that raises the pressure of the liquid to a range of about 3 to 5 bar. Pump 17 to provides the desired liquid velocity to subject the educted gas to high shear forces that dissolves some of the gas and generates relatively fine microbubbles (0.1 to 1.0 mm in diameter) with the remainder of the gas. Ejection of this mixture from the contact chamber 23 into the fermentation vessel creates a plume 21 that typically enters the fermentation vessel horizontally or at a slight downward angle. The force of the plume creates eddy currents in the surrounding liquid thoroughly mixing the contents of the fermentation vessel. As the plume dissipates, the gas bubbles rise to the liquid surface providing additional mixing and gas dissolution.

A 36 $m^3$ fermenter in the form of a fermentation vessel having a 1.5 meter diameter and a 20 meter wetted depth is used as a MBBR for the conversion of carbon monoxide and hydrogen into ethanol. The fermenter is filled approximately 50% of the liquid working volume with AnoxKaldnes K1 media. A gas of about 40% CO, 30% $H_2$, and 30% $CO_2$ is fed to the vessel at 3.5 $m^3$ per minute and 3 bar absolute inlet pressure and the residual gas exits the module at less than 0.1 bar outlet pressure. This gas flow is added to a slot aeration/gas transfer device operated at a liquid recycle flow rate of 400 liters per minute. The fermentation medium having the composition given in Table 2 is used to fill the fermenter and maintained at about 37degrees c. The fermenter is maintained under anaerobic conditions.

The fresh fermentation medium contains the components listed in Tables 2 & 3(a)-(d). Initially, the bioreactor process is operated in the batch mode and inoculated with 2000 liters of an active culture of *Clostridium ragsdalei* ATCC No. BAA-622. The fermentation pH is controlled at pH 5.9 in the first 24 hours by addition of 1 N $NaHCO_3$ to favor cell growth and then allowed to drop without control until it reaches pH 4.5 to favor ethanol production. The process remains in the batch mode for 1 day to establish the attachment of the microbial cells on the media surface. Then, the process is switched to continuous operation, with continuous withdrawal of the fermentation broth for product recovery and replenish of fresh medium. With the continuous operation, suspended cells in the fermentation broth are gradually removed from the bioreactor process and decrease in concentration, while the biofilm attached on the media continues to grow until the biofilm reaches a thickness equilibrated with the operating conditions. The ethanol concentration at the end of the 10-day batch operation is 5 g/L. At the beginning of the continuous operation, a low broth withdrawal rate is selected so that the ethanol concentration in the broth does not decrease but increases with time. The broth withdrawal rate is then gradually increased. After 30 days of continuous operation, the ethanol concentration increases to 30 g/L with the broth withdrawal rate at 22 liters per minute. The attached cell concentration is approximately 5 g/L dry weight at this point in time.

TABLE 2

Fermentation Medium Compositions

| Components | Amount per liter |
|---|---|
| Mineral solution, See Table 3(a) | 25 ml |
| Trace metal solution, See Table 3(b) | 10 ml |
| Vitamins solution, See Table 3(c) | 10 ml |
| Yeast Extract | 0.5 g |
| Adjust pH with NaOH | 6.1 |
| Reducing agent, See Table 3(d) | 2.5 ml |

TABLE 3(a)

Mineral Solution

| Components | Concentration (g/L) |
|---|---|
| NaCl | 80 |
| $NH_4Cl$ | 100 |

TABLE 3(a)-continued

Mineral Solution

| Components | Concentration (g/L) |
|---|---|
| KCl | 10 |
| $KH_2PO_4$ | 10 |
| $MgSO_4 \cdot 7H_2O$ | 20 |
| $CaCl_2 \cdot 2H_2O$ | 4 |

TABLE 3(b)

Trace Metals Solution

| Components | Concentration (g/L) |
|---|---|
| Nitrilotriacetic acid | 2.0 |
| Adjust the pH to 6.0 with KOH | |
| $MnSO_4 \cdot H_2O$ | 1.0 |
| $Fe(NH_4)_2(SO_4)_2 \cdot 6H_2O$ | 0.8 |
| $CoCl_2 \cdot 6H_2O$ | 0.2 |
| $ZnSO_4 \cdot 7H_2O$ | 1.0 |
| $NiCl_2 \cdot 6H_2O$ | 0.2 |
| $Na_2MoO_4 \cdot 2H_2O$ | 0.02 |
| $Na_2SeO_4$ | 0.1 |
| $Na_2WO_4$ | 0.2 |

TABLE 3(c)

Vitamin Solution

| Components | Concentration (mg/L) |
|---|---|
| Pyridoxine HCl | 10 |
| Thiamine HCl | 5 |
| Roboflavin | 5 |
| Calcium Pantothenate | 5 |
| Thioctic acid | 5 |
| p-Aminobenzoic acid | 5 |
| Nicotinic acid | 5 |
| Vitamin B12 | 5 |
| Mercaptoethanesulfonic acid | 5 |
| Biotin | 2 |
| Folic acid | 2 |

TABLE 3(d)

Reducing Agent

| Components | Concentration (g/L) |
|---|---|
| Cysteine (free base) | 40 |
| $Na_2S \cdot 9H_2O$ | 40 |

The invention claimed is:

1. A process for converting a feed gas containing at least one of CO, $H_2$, $CO_2$ and a mixture of $CO_2$, $H_2$ and CO to a liquid product, said process comprising:

a) passing a feed gas into a vessel that retains a fermentation broth and microorganisms therein under anaerobic conditions with the fermentation broth supplying nutrients to the microorganisms that produce a liquid product from the feed gas, wherein an injector at least partially entrains the feed gas in a liquid medium as microbubbles before the feed gas enters the vessel;

b) delivering the entrained feed gas and liquid medium to the fermentation broth as a plume wherein the plume is injected into the vessel in a substantially horizontal direction and the plume travels upwardly and horizontally through the vessel after the substantially horizontal injection of the plume from the injector, so that at least a part of the plume travels in a horizontal direction at least half way across the vessel so that the broth and microorganisms receive feed gas across the full cross section of the vessel;

c) retaining inert microorganism carriers having a surface supporting a biofilm of the microorganisms in the vessel, wherein said carriers are arranged for circulation throughout the fermentation broth in the vessel;

d) circulating the carriers containing the microorganisms and the broth in the vessel, so that a portion of the carriers and the broth directly contacts the plume at the location where the plume enters the vessel in the substantially horizontal direction;

e) withdrawing the fermentation broth containing the liquid products from the vessel through a carrier retainer to impede the withdrawal of the carriers with the broth; and, f) recovering the liquid product from the withdrawn broth.

2. The process of claim 1 wherein injector comprises a contact chamber, at least a portion of the liquid medium comprises the fermentation broth, and the plume is injected from the contact chamber into the vessel, wherein said plume comprises a mixture of the microbubbles and a liquid containing dissolved feed gas.

3. The process of claim 2 wherein the plume provides a mixing intensity that controls the thickness of the biofilm on the carriers.

4. The process of claim 1 wherein at least a portion of the plume, after the substantially horizontal injection, changes direction and travels vertically through the fermentation broth for a distance of at least 9 meters.

5. The process of claim 1 wherein the carriers have a relative density of 0.9 to 0.98 with respect to the fermentation broth.

6. The process of claim 1 wherein the carriers fill at least 30 to 70% of a wetted volume of the vessel.

7. The process of claim 1 wherein the liquid product comprises at least one of ethanol, n-butanol, acetic acid and butyric acid.

8. The process of claim 1 wherein the microorganisms comprises a mono-culture or a co-culture of any of Clostridium ragsdalei, Butyribacterium methylotrophicum, Clostridium Ljungdahl, Clostridium autoethanogenum, or Clostridium Coskatii.

9. The process of claim 1 wherein the carriers have a ratio of protected surface to total surface of at least 60%.

10. The process of claim 1 wherein the microbubbles have a diameter of from 0.1 to 1.0 mm.

* * * * *